Figure 1:
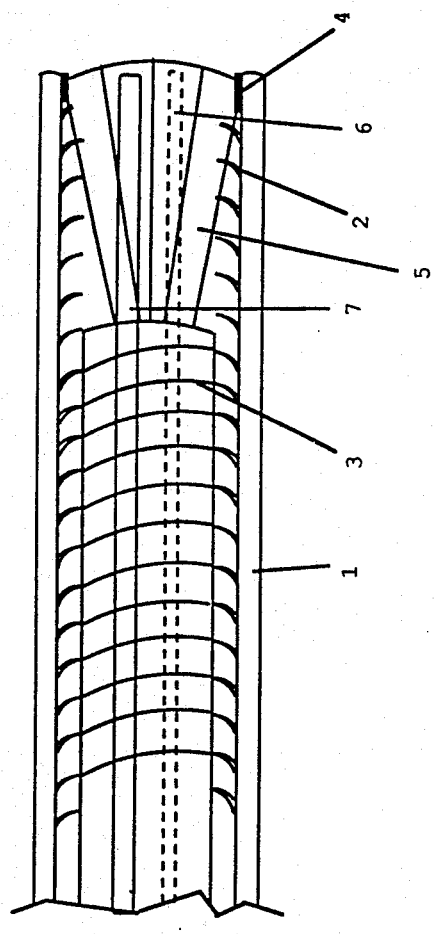

United States Patent [19]

Stiles

[11] Patent Number: 4,692,139

[45] Date of Patent: Sep. 8, 1987

[54] CATHETER FOR EFFECTING REMOVAL OF OBSTRUCTIONS FROM A BIOLOGICAL DUCT

[76] Inventor: Frank B. Stiles, P.O. Box 41, Carp, Ontario, Canada, K0A 1L0

[21] Appl. No.: 781,927

[22] Filed: Sep. 30, 1985

[30] Foreign Application Priority Data

Mar. 9, 1984 [CA] Canada ................................ 449331

[51] Int. Cl.$^4$ .............................................. A61M 1/00
[52] U.S. Cl. ...................................... 604/22; 604/19; 604/35; 604/42; 604/93; 604/109
[58] Field of Search ....................... 604/22, 19, 35, 42, 604/51, 52, 53, 93, 104, 109, 117, 241, 890, 107, 106, 108, 109, 271; 128/772, 7

[56] References Cited

U.S. PATENT DOCUMENTS

| | | | |
|---|---|---|---|
| 3,589,363 | 6/1971 | Banko et al. | 604/8 |
| 3,792,701 | 2/1974 | Kloz et al. | 128/7 |
| 3,913,565 | 10/1975 | Kawahara | 128/772 |
| 4,041,947 | 8/1977 | Weiss et al. | 604/51 |
| 4,063,557 | 12/1977 | Wuchinich et al. | 604/22 |
| 4,078,564 | 3/1978 | Spina et al. | 604/51 |
| 4,466,435 | 8/1984 | Murray | 128/303 R |
| 4,515,583 | 5/1985 | Sorich | 604/22 |
| 4,516,398 | 5/1985 | Wuchinich | 604/22 |
| 4,526,571 | 7/1985 | Wuchinich | 604/22 |
| 4,531,934 | 7/1985 | Kossovsky | 604/22 |
| 4,561,446 | 12/1985 | Hetz | 128/7 |

FOREIGN PATENT DOCUMENTS 866946 3/1971 Canada .
1078925 6/1980 Canada .

Primary Examiner—Stephen C. Pellegrino
Assistant Examiner—John D. Ferros
Attorney, Agent, or Firm—Pascal & Associates

[57] ABSTRACT

A catheter for insertion into a biological duct such as an artery, comprised of a flexible aspiration tube disposed within a delivery sleeve and connected at one end to a source of vacuum for providing suction within the duct in the vicinity of a biological obstruction, such as a blood clot. An injection tube extends through the aspiration tube for injecting medication into the duct, and an ultrasonic energy source also extends through the aspiration tube for transmitting ultrasound in the vicinity of the obstruction. The transmitted ultrasound and injected medication cooperate to emulsify and fragment the obstruction, and the fragmented obstruction is removed through the aspiration tube in response to suction being applied thereto. The catheter is compact and easily manipulable, providing substantial surgical accuracy.

25 Claims, 5 Drawing Figures

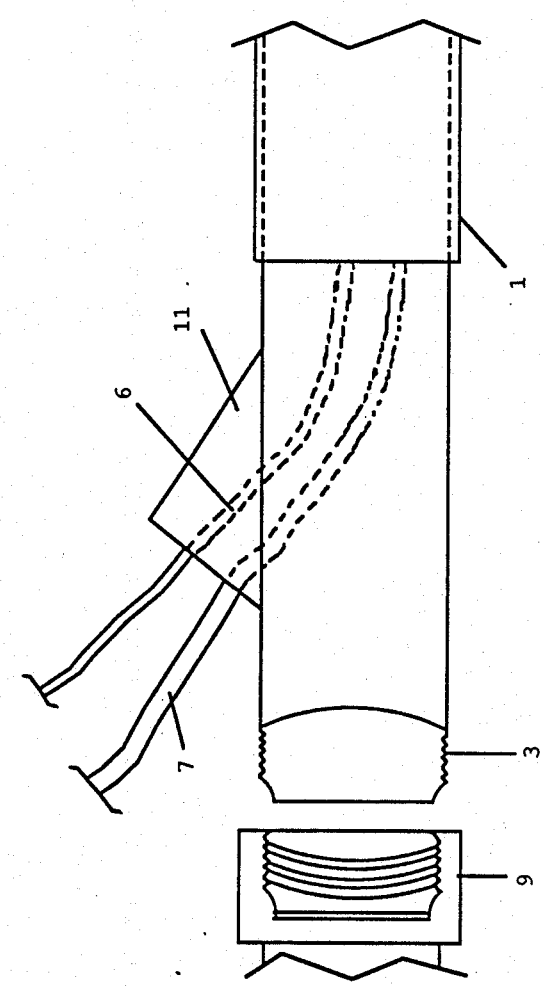

CATHETER FOR EFFECTING REMOVAL OF OBSTRUCTIONS FROM A BIOLOGICAL DUCT

This invention relates in general to surgical instruments, and in particular to a catheter for insertion into a biological duct in order to effect removal of obstructions therefrom.

Prior art surgical devices are well known for disintegrating obstructions such as stones or concretions from the urinary track as well as plaque and sclerotic clots in other human ducts such as arteries. Canadian patent No. 866,946 entitled INSTRUMENT FOR CRUSHING STONES IN THE URINARY BLADDER, issued Mar. 23, 1971 to Balaev et al teaches an electrical device for discharging electrical pulses in a gap between a pair of electrodes surrounding an obstruction. The impact of the electrical discharge causes the obstruction to disintegrate. However, no means are taught for removing the fragmented obstruction. Also, it has been found that such electrical discharges can burn or otherwise damage surrounding biotissue.

Likewise, Canadian patent No. 1,078,925 entitled CALCULI DISINTEGRATING APPRATUS, issued June 3, 1980 to Calculus Instruments Limited, teaches a surgical device having positive and negative electrodes for effecting an electrical discharge in conjunction with application of a liquid, in order to disintegrate an obstruction via hydro-electric action. The Calculus Instrument device utilizes a harp distender for distending the duct walls to reduce burning and shock damage to the skin as a result of the electric discharge. Notwithstanding utilization of the harp distender, it has been found that prior art electric discharge devices such as those disclosed in the Balaev et al and Calculus Instruments patents, produce considerable trauma in the human body.

Surgical instruments are also well known for aspirating specific regions of a body cavity in order to remove residual matter. One such device is described in Canadian patent No. 1,006,231 issued Mar. 1, 1977 to Durden, which teaches the use of a suction tube in a cauterizing instrument.

Advances in the surgical arts have led to the use of ultrasound for fragmenting obstructions, which has been found to be substantially less traumatic to the human body than prior art electrical discharge apparatus. In order to enhance the obstruction disintegration properties of ultrasound, it has been contemplated that medication, such as an enzyme, may be simultaneously injected in the vicinity of the obstruction. A device utilizing ultrasound is described in Canadian patent No. 1,092,657 entitled DEVICE AND METHOD FOR APPLYING PRECISE IRRIGATION, ASPIRATION, MEDICATION, ULTRASONIC POWER AND DWELL TIME TO BIOTISSUE FOR SURGERY AND TREATMENT issued Dec. 30, 1980 to Fibra-Sonics, Inc. The Fibra-Sonics device utilizes two separate ducts disposed in two separate needles for providing irrigation and aspiration in conjunction with ultrasound. According to the Fibra-Sonics device an irrigation needle is inserted directly into the human body by applying ultrasound to the needle in order to make an incision in the immediate vicinity of the obstruction. The forceful injection of dissolvents by means of the inserted needle in conjunction with bursts of ultrasound transmitted through the needle results in rapid emulsification of the obstruction. A separate aspiration needle is also inserted into the body in the vicinity of the obstruction, via a separate incision, in order to remove the fragmented obstruction and any residual medication. In the event the area surrounding the obstruction is not adequately aspirated, fragments and residual medication can migrate through the circulatory system which may lead to a critical situation in the event the medication is an enzyme for dissolving blood clots, since the enzyme would damage heart tissue if not immediately removed. However, since two incisions are made the fragments and residual medication are not confined to within the biological duct (such as an artery) but may inadvertently spill out from the duct through one or both of the incisions. Thus, great care must be taken when utilizing the Fibra-Sonics device to ensure adequate aspiration. Thus, while it is known to use aspiration in surgery (as taught by either Durden or Fibra-Sonics) and irrigation with ultrasound, to fragment or dissolve obstructions (as taught by Fibra-Sonics) it has not hitherto been known to simultaneously incorporate irrigation, aspiration and ultrasound in a single unitary surgical instrument. As discussed in the Fibra-Sonics patent, it was believed that incorporation of all three functions in a single instrument, requiring at least two adjacent ducts (one for aspiration and one for medication), would result in severe trauma, since a large incision would be required.

According to the present invention, a device is provided for integrating the functions of aspiration, irrigation and ultrasound application within a single catheter, for insertion into a biological duct via a single incision remote from the vicinity of the obstruction and moved into position within the duct. Thus, irrigation, ultrasound generation and aspiration occur within the confines of the biological duct and are localized in the vicinity of the obstruction. Hence, fragments and residual medication are immediately and easily removed without risk of spreading to other parts of the body through the circulatory system. Thus, the present invention overcomes the disadvantages of Calculus Instruments and Balaev et al which required traumatic electro shock treatment to disintegrate obstructions, yet also overcomes the disadvantage of Fibra-Sonics or Durden which require incisions to be made in the human body.

In general, the invention is a catheter for effecting removal of obstructions from a biological duct, comprising a flexible aspiration tube for insertion into the duct such that a first end thereof is disposed in the vicinity of the obstruction and on opposite end thereof is connectable to a source of vacuum for providing suction within the duct at the first end in the vicinity of the obstruction, an injection tube disposed within the aspiration tube for injecting medication into the duct in the vicinity of the obstruction, and an ultrasonic energy source for transmitting ultrasound through the aspiration tube in the vicinity of the obstruction. The ultrasound and medication cooperate to emulsify and fragment the obstruction, and the emulsified and fragmented obstruction is removed from the duct through the aspiration tube in response to suction being provided.

The invention is also a method of fragmenting and removing obstructions from a biological duct, comprising the steps of inserting a catheter into the duct, deploying an aspiration tube housed within the catheter and including a medication tube and ultrasonic energy source, to a position externally of an open end of the catheter in the vicinity of the obstruction, and injecting medication and transmitting ultrasonic energy via the medication tube and ultrasonic energy source respectively in the vicinity of the obstruction for emulsifying and fragmenting the obstruction, and simultaneously vacuuming the vicinity to remove emulsified fragments of the obstruction and residual medication via the aspiration tube.

Figure 2:
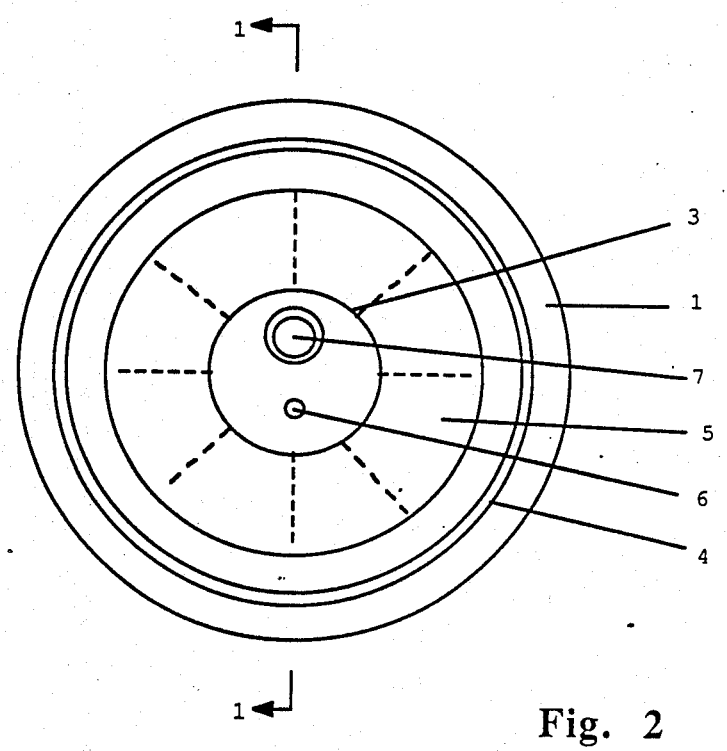
Figure 3:
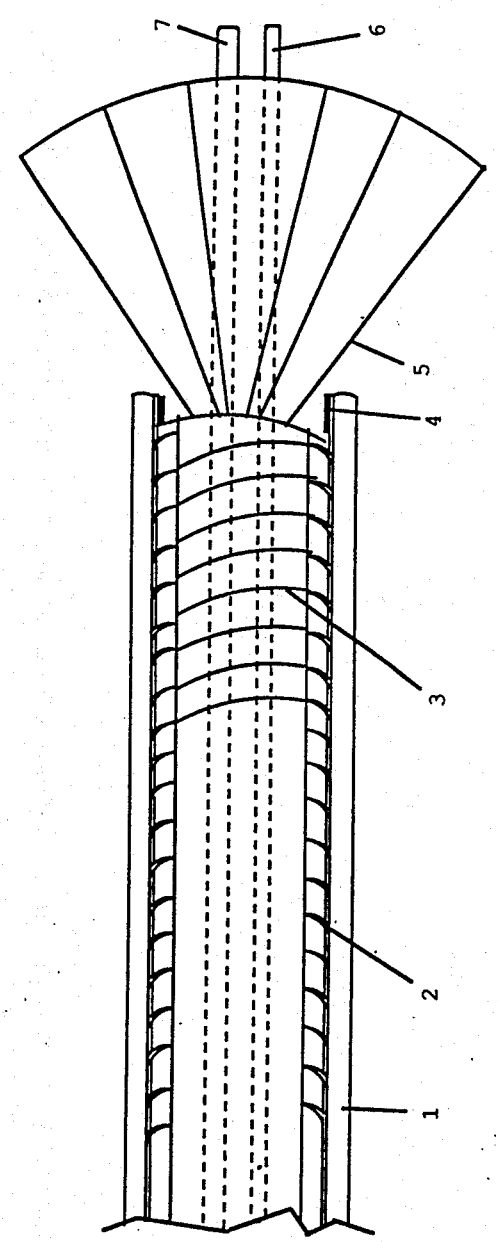

A better understanding of the present invention will be obtained with reference to the detailed description below in conjunction with the following drawings, in which:

FIG. 1 is a longitudinal cross sectional view of a catheter according to the present invention, taken along the line 1—1 shown in FIG. 2, FIG. 2 is an end view of the catheter according to the present invention, FIG. 3 is a longitudinal cross sectional view of the catheter in a deployed position, taken along the line 1—1 in FIG. 2, and FIGS. 4A and 4B are longitudinal cross sectional views of apparatus for coupling an opposite end of the catheter to a source of vacuum.

With reference to FIG. 1 a catheter is shown comprised of a flexible delivery sleeve 1 having a threaded inner wall 2. Disposed within the delivery sleeve is an aspiration tube 3 having a fine gauge male thread on an outer wall thereof, matching the fine gauge female thread 2.

By turning the aspiration tube 3 clockwise within the delivery sleeve 1, the aspiration tube 3 is caused to move towards an open end of the delivery sleeve 1, due to the action of the cooperating threads. An inner blocking ring 4 is located at the open end of the delivery sleeve 1 for limiting the movement of the aspiration tube 3 to an optimum position at the open end of the delivery sleeve.

Mounted on a remote end of aspiration tube 3 is a folded soft springy rubber shield 5. The shield 5 is shown in a collapsed retracted position within the flexible delivery sleeve 1. An ultrasound probe 6 and medication injection tube 7 are disposed within the aspiration tube 3 and have remote ends thereof located at the open end of delivery sleeve 1.

Turning to FIG. 2, the position of medication injection tube 7 and ultrasound probe 6 disposed within aspiration tube 3, is shown in greater detail.

In FIG. 3, the aspiration tube 3 is shown in a deployed position, having been turned clockwise within delivery sleeve 1 to a position in abutment with blocking ring 4. In this position, medication injection tube 7 and ultrasound probe 6 extend beyond the open end of the delivery sleeve 1, and shield 5 is shown in an expanded deployed position. The shield 5 opens and closes between the deployed and retracted positions with an action similar to that of opening and closing an umbrella.

Referring to FIGS. 4A and 4B, a base end of the aspiration tube 3 extends from the base end of delivery sleeve 1, and has fine gauge male threads disposed on an outer wall thereof for coupling with fine gauge female threads disposed within an inner wall of a sealed coupler 9 for coupling the aspiration tube 3 to a source of vacuum, (not shown) such as a well known variable range AC/DC powered vacuum pump including rate controls, foot pedal action controls and a sterile container for receiving the removed fragments in order to facilitate biopsy analysis.

A sealed junction 11 projects from the outer wall of aspiration tube 3, and the ultrasonic probe 6 and medication injection tube 7 extend therethrough for connection to an external ultrasound energy source and a source of medication, respectively.

The source of medication is preferably an injector syringe, automatic AC/DC peristaltic pump or other device for propelling medication, such as an enzyme, through the injection tube 7 at a predetermined rate and pressure, which preferably can be either steady or pulsating.

The ultrasonic energy source is preferably a well known adjustable, multi-high range frequency AC/DC resonator or oscillator.

The delivery sleeve 1, aspiration tube 3 and medication injection tube 7 are preferably fabricated from high quality surgical plastic.

In order to emulsify and fragment an obstruction such as a blood clot blocking the coronary artery or other artery chambers of the heart, the delivery sleeve 1 is preferably inserted into an appropriate leg artery according to well known surgical techniques, and is fed through the artery to a position within the coronary artery or artery chamber in close proximity to the obstruction.

With the delivery sleeve in place, and the base end thereof projecting outwardly from the leg artery, the aspiration tube 3 is turned clockwise at the base end. In response, the aspiration tube 3 moves to the deployed position as illustrated by FIG. 3, wherein the blocking ring 4 prevents the aspiration tube 3 from extending beyond the end of the delivery sleeve 1. The rubber shield 5 expands and the ultrasonic probe 6 and medication injection tube 7 extend from the end of the sleeve 1 so as to be preferably in close proximity to the obstruction.

The aspiration tube 3 is then coupled at the base end via coupling 9 by rotating the coupling such that the mutual threads of the coupling 9 and aspiration tube 3 cooperate to draw the tube into air-tight engagement with the source of vacuum.

As discussed above, the ultrasonic probe 6 extending outwardly from junction 11, is connected to the source of ultrasonic energy, which preferably has a foot control pedal for controlling the frequency and intensity of the energy, and preferably generates signals having frequencies of at least 60 kilohertz.

The medication injection tube 7 extending from junction 11 is then connected to the source of medication such as the aforementioned automatic adjustable injection pump. As discussed above, the pump is preferably capable of accommodating multiple rate fixed, steady or pulsating action for propelling controlled volumes of medication such as enzymes in an oxygen enriched saline solution, or otherwise, down the tube 7 at a predetermined rate of fixed, steady or pulsating volume, concentration, speed and pressure.

According to a preferred use of the present invention for emulsifying blood clots, an enzyme such as streptokinase, t-PA, etc., with or without a blood plasma or saline carrier, is injected into the coronary artery for causing the blood clot to emulsify and fragment.

The accompanying ultrasonic energy transmitted via ultrasound probe 6 serves to accelerate the emulsifying and fragmenting action caused by application of the enzyme, and with the source of vacuum set at a predetermined rate above normal blood flow pressure, the fragments and residual enzymes are collected and removed via aspiration tube 3. The shield 5 serves to direct the movement of the fragments and residual enzymes into the aspiration tube 3. Clot dissolving enzymes can cause damage to heart tissues, and it has been found that by aspirating the area surrounding the fragmented clot so as to remove the residual enzymes and prevent them from passing through the general vascular blood stream of the patient, such damage is substantially eliminated. Thus, higher concentration enzymes and other medication may be used in the present invention than in prior art devices since the highly efficient aspiration process ensures that the residual medication does not spread to other parts of the body.

Once the clot has been removed, the ultrasonic probe 6, injection tube 7 and aspiration tube 3 are disconnected at the base end and the aspiration tube 3 is turned counter-clockwise so as to move the shield 5, probe 6 and tube 7 into a retracted position within the delivery sleeve 1, as illustrated by FIG. 1. The delivery sleeve 1 is then withdrawn from the patient's body in a straight forward well known manner.

According to the present invention, it has been found that a blood clot will emulsify, fragment and be removed in approximately no more than two and one-half minutes. Because speed is of the essence when removing a blood clot or in the event of a heart attack, the present invention has been found to be a unique improvement over prior art devices. Also, by removing blood clot fragments by aspiration, the fragments are prevented from travelling through the patient's circulatory system to the lungs or brain which otherwise could cause brain damage or stroke, etc. Further, as a result of integrating the aspiration tube, medication irrigation tube, ultrasound probe and shield in a single catheter, stronger and more effective enzymes may be applied in the vicinity of an obstruction which, in the absence of efficient aspiration, would overthin a patient's blood which can be dangerous in the event of imminent surgery. By fragmenting and removing obstructions in such a rapid and effective manner oxygen is rapidly restored to the heart muscles and related tissues, thereby preventing irreversible heart damage, etc.

A person skilled in the art understanding the present invention may conceive of further embodiments or variations using the principles disclosed herein. For instance, by slightly modifying the dimensions of the present device, it can be used to remove cataracts from the eyes, bladder stones from the urinary system, and other obstructions from various internal biological ducts without requiring major surgery. Also, while ultrasonic probe 6 has been shown in the drawings (FIG. 2) as being of circular cross section, it can alternatively be made of square cross section.

All these and other modifications or variations are considered to be within the sphere and scope of this invention as defined in the claims appended hereto.

I claim:

1. A catheter for effecting removal of obstructions from a biological duct, comprising a flexible aspiration tube for insertion into said duct such that a first end thereof is disposed in the vicinity of said obstruction and an opposite end thereof is connectable to a source of vacuum for providing suction within said duct at said first end in the vicinity of said obstruction, an injection tube disposed within said aspiration tube for injecting medication into said duct in the vicinity of said obstruction, and an ultrasonic energy source for transmitting ultrasound through said aspiration tube to the vicinity of said obstruction, whereby said ultrasonic energy and medication cooperate to emulsify and fragment said obstruction and the emulsified and fragmented obstruction is removed from said duct through the aspiration tube in response to suction being provided by said source of vacuum, and further including a flexible delivery sleeve enveloping said aspiration tube and screw threaded thereto at said first end, said aspiration tube being movable between extended and retracted positions relative to said sleeve by rotation therein.

2. A catheter as defined in claim 1, further including a collapsible shield connected to said first end of the aspiration tube, said shield being movable between a collapsed position within said delivery tube and a deployed position externally of said delivery tube in response to said aspiration tube being moved between said retracted and extended positions respectively, whereby in said deployed position the shield directs removal of said fragmented matter from said vicinity into the aspiration tube.

3. A catheter as defined in claim 2 wherein said shield is fabricated from flexible rubber.

4. A catheter as defined in claim 2 further including a blocking ring disposed on an inner surface of said delivery sleeve at said first end, for limiting movement of said aspiration tube between said retracted position and a predetermined optimum extended position.

5. A catheter as defined in claim 2, wherein said ultrasonic energy source is comprised of a variable frequency ultrasonic oscillator connected at said opposite end of the aspiration tube to an ultrasonic probe extending therethrough and terminating at said first end.

6. A catheter as defined in claim 2, wherein said ultrasonic energy source is comprised of a variable frequency ultrasonic oscillator connected at said opposite end of the aspiration tube to an ultrasonic probe having substantially square cross section and extending through said aspiration tube and terminating at said first end.

7. A catheter as defined in claim 2 wherein said source of vacuum is a vacuum pump.

8. A catheter as defined in claim 2, wherein said source of vacuum is a vacuum pump and said aspiration tube is connected at said opposite end thereto via mutual threading disposed within an air-tight sealed coupler.

9. A catheter as defined in claim 2, wherein said injection tube is connected at said opposite end to an injector syringe.

10. A catheter as defined in claim 2, wherein said injection tube is connected at said opposite end to an automatic AC/DC pump.

11. A catheter as defined in claim 2, wherein said injection tube is connected at said opposite end to means for propelling medication therethrough at one of either a steady speed and pressure or a pulsating speed and pressure.

12. A catheter as defined in claim 2 wherein said delivery sleeve and aspiration tube are fabricated from surgical plastic.

13. A catheter as defined in claim 2, wherein said source of vacuum is a variable range AC/DC powered vacuum pump including rate controls, foot pedal action controls and a sterile container for receiving said removed fragments in order to facilitate biopsy analysis.

14. A catheter as defined in claim 2, wherein said ultrasonic energy source is comprised of an AC/DC powered multi-variable range frequency resonator for generating ultrasonic frequency signals of at least 60 kilohertz frequency.

15. A catheter as defined in claim 1 further including a blocking ring disposed on an inner surface of said delivery sleeve at said first end, for limiting movement of said aspiration tube between said retracted position and a predetermined optimum extended position.

16. A catheter as defined in claim 1 wherein said delivery sleeve and aspiration tube are fabricated from surgical plastic.

17. A catheter as defined in claim 1, wherein said ultrasonic energy source is comprised of a variable frequency ultrasonic oscillator connected at said opposite end of the aspiration tube to an ultrasonic probe extending therethrough and terminating at said first end.

18. A catheter as defined in claim 2, wherein said ultrasonic energy source is comprised of a variable frequency ultrasonic oscillator connected at said opposite end of the aspiration tube to an ultrasonic probe having substantially square cross section and extending through said aspiration tube and terminating at said first end.

19. A catheter as defined in claim 1 wherein said source of vacuum is a vacuum pump.

20. A catheter as defined in claim 1, wherein said source of vacuum is a vacuum pump and said aspiration tube is connected at said opposite end thereto via mutual threading disposed within an air-tight sealed coupler.

21. A catheter as defined in claim 1, wherein said injection tube is connected at said opposite end to an injector syringe.

22. A catheter as defined in claim 1, wherein said injection tube is connected at said opposite end to an automatic AC/DC pump.

23. A catheter as defined in claim 1, wherein said injection tube is connected at said opposite end to means for propelling medication therethrough at one of either a steady speed and pressure or a pulsating speed and pressure.

24. A catheter as defined in claim 1, wherein said source of vacuum is a variable range AC/DC powered vacuum pump including rate controls, foot pedal action controls and a sterile container for receiving said removed fragments in order to facilitate biopsy analysis.

25. A catheter as defined in claim 1, wherein said ultrasonic energy source is comprised of an AC/DC powered multi-variable range frequency resonator for generating ultrasonic frequency signals of at least 60 kilohertz frequency.

* * * * *